United States Patent [19]

Kanesaka

[11] Patent Number: 5,042,470
[45] Date of Patent: Aug. 27, 1991

[54] VENTILATING SYSTEM FOR RESPIRATION OF A PATIENT

[76] Inventor: Nozomi Kanesaka, 37 Forest Dr., Plainview, N.Y. 11803

[21] Appl. No.: 358,075

[22] Filed: May 30, 1989

[51] Int. Cl.$^5$ ............................................. A61M 16/00
[52] U.S. Cl. ........................... 128/202.22; 128/204.18; 128/204.21; 128/205.23
[58] Field of Search ...................... 128/202.22, 204.18, 128/204.21, 204.23, 205.23, 203.12

[56] References Cited

U.S. PATENT DOCUMENTS

| | | | |
|---|---|---|---|
| 2,828,741 | 4/1958 | Delest | 128/202.22 |
| 3,147,499 | 9/1964 | Nelson et al. | 128/202 22 |
| 3,508,542 | 4/1970 | Browner | 128/202.22 |
| 4,064,875 | 12/1977 | Cramer et al. | 128/202.22 |
| 4,250,876 | 2/1981 | Kranz | 128/202.22 |
| 4,323,064 | 4/1982 | Hoenig et al. | 128/202.22 |
| 4,423,723 | 1/1984 | Winkler et al. | 128/202.22 |
| 4,766,894 | 8/1988 | Legrand et al. | 128/202.22 |
| 4,870,960 | 10/1989 | Hradek | 128/202.22 |

Primary Examiner—Aaron J. Lewis
Attorney, Agent, or Firm—Kanesaka and Takeuchi

[57] ABSTRACT

The present invention relates to a ventilating system adapted to supply breathing gas to a patient and exhaust used gas therefrom. The ventilating system comprises a main ventilating device for supplying breathing gas to a patient, detecting device for detecting malfunction of the main ventilating device, and an auxiliary ventilating device. The auxiliary ventilating device includes a hollow tube installed along a connector of the main ventilating device and an auxiliary breathing gas supply device connected to the hollow tube. When the detecting device detects malfunction of the main ventilating device, the auxiliary ventilating device automatically actuates to supply breathing gas to the patient.

3 Claims, 3 Drawing Sheets

VENTILATING SYSTEM FOR RESPIRATION OF A PATIENT

BACKGROUND OF THE INVENTION AND RELATED ART STATEMENT

The present invention relates to a ventilating system for respiration of a patient with an auxiliary ventilating device.

A ventilating system or a ventilator has been used for helping respiration of a patient, who is treated with operation under whole anesthesis or has a breathing disorder.

There are two kinds of ventilators known already. A first one is a general type to supply necessary amount of breathing gas periodically to a patient through a tracheal tube or a mask. This ventilator operates periodically similar to a function of a lung of a patient to help breathing of a patient. Namely, a compressed breathing gas is supplied to and exhausted from a lung of a patient according to a function of a lung. This type of ventilator is widely used because it simulates natural function of a lung.

A second type of a ventilator is to supply a small amount of compressed breathing gas to a lung at a rate of 30 times or more per one minute. The amount of breathing gas to be supplied is determined based on the patient condition. In this ventilator, it is designed that oxygen exchange function of a lung only occurs. Namely, in this ventilator, breathing gas is forcibly supplied to a lung to exchange oxygen thereat without physical movement of a lung.

In this second type of the ventilator, a small tube is installed in a tracheal tube. A compressed breathing gas is supplied to a lung through the small tube, and the used gas is exhausted through the tracheal tube.

In the ventilators as stated above, alarm systems are generally provided so that if the ventilators do not operate properly, mulfunction of the ventilators is noticed. Even if alarm systems are installed, however, unless the alarm systems are monitered, the mulfunction of the ventilators can not be noticed. Further, in case mulfunction of a ventilator is noticed, the ventilator must be immediately fixed or exchanged with a new ventilator, which can not be done easily at a side of a patient.

A ventilator must be attached to a mouth of a patient. Therefore, it is difficult to install two ventilators so that one ventilator constitutes a support system.

Accordingly, one object of the invention is to provide a ventilating system with an auxiliary ventilating device so that in case a main ventilating device does not work, the auxiliary ventilating device automatically starts to operate to provide breathing gas to a patient.

Another object of the invention is to provide a ventilating system as stated above, wherein the auxiliary ventilating device can be easily installed in a main ventilating system without causing trouble to a patient and the main ventilating device.

A further object of the invention is to provide a ventilating system as stated above, wherein the auxiliary ventilating device can be easily installed in a conventional ventilating system operating as a main ventilating device.

Further objects and advantages of the invention will be apparent from the following description of the invention.

SUMMARY OF THE INVENTION

In accordance with the present invention, a ventilating system for supplying breathing gas to a patient and exhausting used gas therefrom is provided. The ventilating system comprises a main ventilating device to supply breathing gas to a patient, a detecting device attached to the main ventilating device for detecting mulfunction of the main ventilating device, and an auxiliary ventilating device to supply breathing gas only when the main ventilating devices does not operate.

The main ventilating device comprises a connector adapted to be inserted into a throat of a patient, and breathing gas supply means connected to the connector to supply breathing gas to the patient through the connector. An exhaust device is attached to the connector to exhaust used gas to outside.

The auxiliary ventilating device includes a hollow tube installed either inside or along side of the connector, and an auxiliary breathing gas supply means connected to the hollow tube. When the detecting device detects mulfunction of the main ventilating device, the auxiliary ventilating device automatically actuates to supply breathing gas to the patient through the hollow tube.

The connector of the main ventilating device may be a tracheal tube insearted into a throat of a patient. Preferably, the hollow tube is retained inside the tracheal tube. Compressed breathing gas is supplied through the hollow tube to the patient. The used gas is exhaust from the patient through the tracheal tube.

The detecting device may include an alarm device for alarming mulfunction of the main ventilating device. The auxiliary ventilating device is actuated automatically when the alarm device is actuated. The auxiliary ventilating device includes an auxiliary exhaust device attached to the connector to exhaust used gas from a lung of the patient. Accordingly, gas supplied from the auiliary ventilating device and used by the patient can be exhausted safely.

DETAILED DESCRIPTION OF PREFERRED EMBODIMENT

Figure 1:
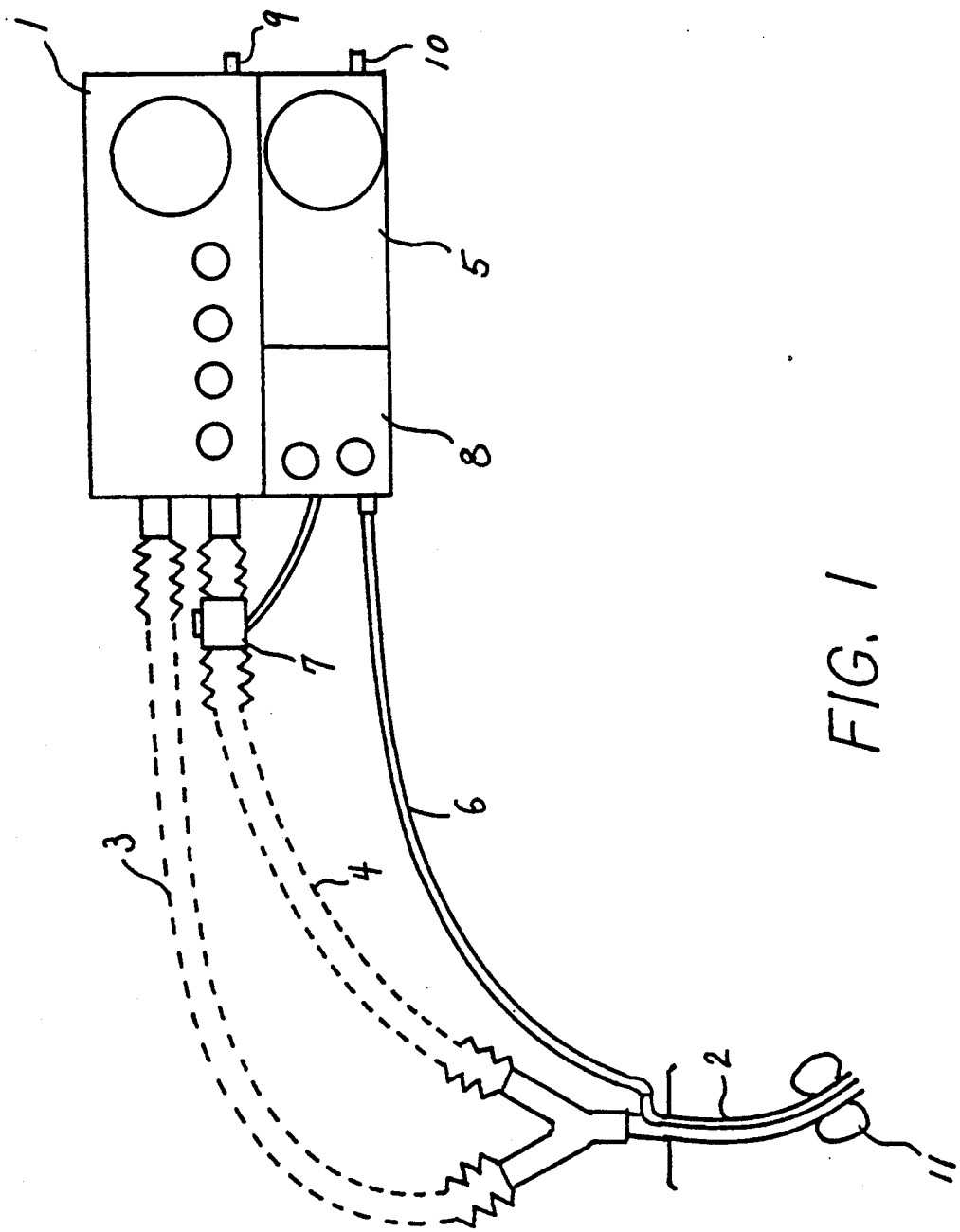
FIG. 1 is an explanatory view of a ventilating system of the present invention.

FIG. 1 shows an explanatory view of a ventilating system of the invention. The ventilating system comprises a main section(1) for supplying breathing gas, such as air, oxigen, mixture of oxigen and nitride and so on, to a treacheal tube(2) attached to a patient through a connector(3) and receiving used gas from the patient through a connector(4). The ventilating system also includes an auxiliary section(5) for supplying breathing gas to the patient through a hollow tube(6) when the main section(1) accidentally does not work, an exhaust device(7) connected to the connector(4) for exhausting gas supplied by the auxiliary section(5), and a detecting device(8).

The detecting device(8) detects mulfunction of the main section, such as lack of breathing gas, disconnection of the connectors(3) (4), and mechanical mulfunction. Both the main section(1) and the auxiliary section(5) of the ventilating system include separate gas inlets(9) (10).

The auxiliary section(5) comprises a jet ventilator. The jet ventilator works in different principle from the regular ventilator such as the one used as the main section of this ventilating system(1). The jet ventilator injects small amount of high pressured gas (5-9 psi) at 30 to 200 times per minute. A total amount of gas injected per minute (called minute ventilation) should be still equal to the normal ventilation. It only requires the hollow small tube(6) to inject, and the used gas is exhausted from a lung throuth the tracheal tube(2). At the time the gas is being injected, the exhaust mechanism does not have to be closed. Therefore, the exhaust valve does not have to exist and the connector(3) can be used as an exhaust.

Figure 2:
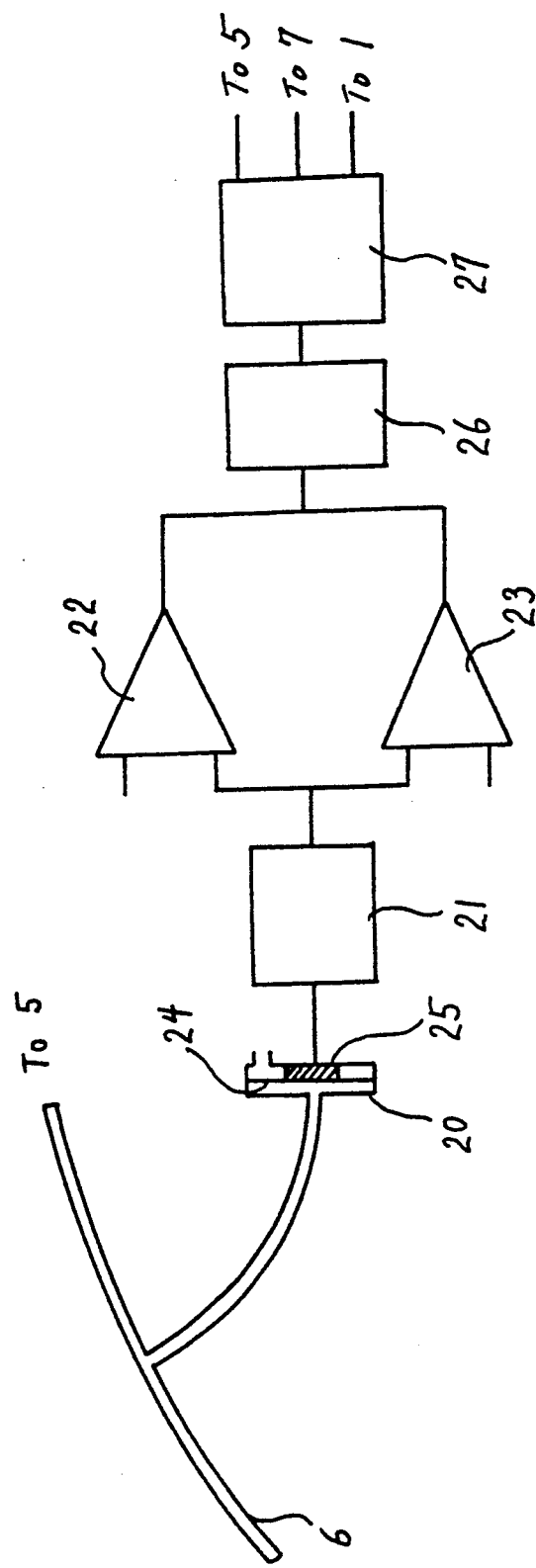
FIG. 2 is an explanatory view of a detecting device for showing the function of the detecting device.

FIG. 2 shows a block diagram of the detecting device(8). The detecting device(8) comprises a pressure transducer(20) for detecting pressure inside the hollow tube(6), an amplifier(21) for amplifing signals generated at the pressure transducer(20), and comparators(22) (23). The best location to monitor pressure in a lung is to directly monitor the pressure, and therefore placing the hollow tube(6) in the tracheal tube(2) adjacent to a lung is almost the ideal location.

The pressure transducer(20) connected to the hollow tube(6) includes a diaphram(24), and a device(25) for converting pressure change into electric signals. Any pressure changes move the diaphram(24) since the other side of the draphram is open to the atmosphere. The device(25) is attached to the diaphram to convert any movement of the diaphram into electric signals, which are then amplified by the amplifire(21).

The amplifier(21) amplifys signals from the device(25) to the comparators(22) (23). The comparator(22) compares signals from the amplifier(21) relative to a high setting value input by an operator, and the comparator(23) compares signals from the amplifier(21) relative to a low setting value input by the operator.

In particular, the comparator(22) provides a high pressure alarm, and the comparator (23) provides a low pressure alarm. Both the high pressure alarm and the low pressure alarm can be set at the desired levels.

The high pressure alarm should be set a little above the maximum infusing pressure, such as 40 cm $H_2O$. The low pressure alarm has two functions. Namely, the first function is that the pressure must come below the set level within certain time period, such as 10 seconds. The second function is that the pressure must exceed over and come back below the set level within certain time period, such as 15 seconds. The second function is also called a dynamic alarm. The following is a list of most common failures and the condition of the alarms.

| MULFUNCTION | HIGH PRESSURE ALARM | LOW PRESSURE ALARM | |
|---|---|---|---|
| | | 1st function | 2nd function |
| Ventilator Failure | — | on | on |
| Disconnect | — | — | on |
| Kink in the circuit | on | — | — |

A time delay circuit(26) for confirming alarming condition for preset time, and a relay(27) are also provided in the detecting device(8). The time delay circuit(26) counts a predetermined time when receiving signals from the comparators(22) (23). Only when the time delay circuit(26) still receives signals from the comparators(22) (23) after a predetermined time has passed since the time delay circuit(26) at first receives signals from the comparaors(22) (23), the relay(27) operates.

The relay(27), when operated, turns on alarm systems, such as audible and visual alarms, terminates the main section(1) of the ventilating system, turns on the auxiliary section(5), and activates the exhaust device(7).

Figure 3:
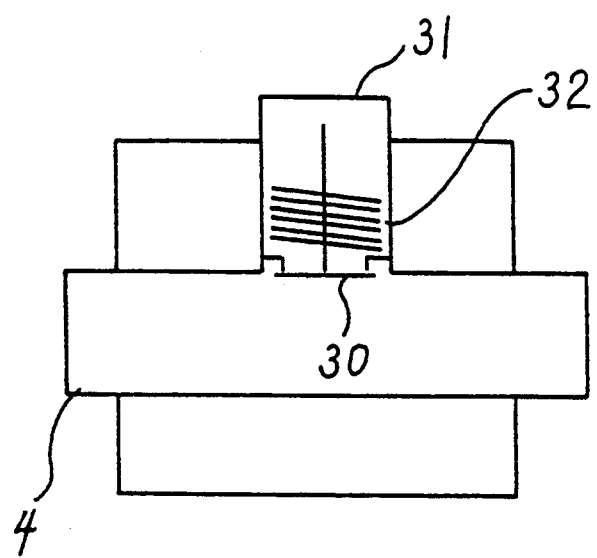
FIG. 3 is an explanatory view of an auxiliary exhaust valve of an auxiliary ventilating device.

FIG. 3 shows an explanatory view of the exhaust device(7). The exhaust device(7) is connected to the connector(4), and includes an exhaust valve(30), an exhaust port(31), and a solenoid(32). The solenoid(32) is activated when the detecting device(8) detects mulfunction of the main section(1) of the ventilating device and opens the exhaust valve(31).

When the ventilating system of the present invention is activated, the main section(1) and auxiliary section(5) must be manually set. Namely, based on a patient weight, height, sex, and other clinical conditions, ventilating pressure, tidal volume, I/E(Inspire/Expire) ratio, frequency of breath, and etc are set at the main section(1) and the auxiliary section(5). When the main section(1) is set, the auxiliary section(5) is automatically set as well.

For example, the main section(1) of the ventilating system can be set to produce a pressure about 10 to 60 cm $H_2O$ at a frequency between 4 to 60 times per minute. A tidal volume can be set between 100 cc to 1600 cc per breath. The are various other settings such as PEEP, CCAP, and etc. These settings may be made based on requirement.

Then, the tracheal tube(2) containing the hollow tube(6), i.e. 2-3 mm O.D., therein is inserted into a patient throat. Thereafter, an inflatable cuff(11) attached to the end of the tracheal tube(2) is inflated to seal and position the tracheal tube(2) in a patient throat.

Ends of the connectors(3) (4) are connected to the tracheal tube(2), and the other ends of the connectors(3) (4) are connected to output and input sides of the main section(1), respectively. Special precaution must be paid for connecting to the proper side of the inspiration and expiration inlets of the ventilator. The hollow tube(6) is connected to the auxiliary section(5), and the exhaust device(7) is connected to the detecting device(8).

When the ventilating system is actuated, the ventilator(1) infuses gas to a patient lung through the connector(3) and the treacheal tube(2) in an inspiratory phase. Once the set amount of gas is infused, the ventilator becomes an expiratory phase, i.e. a patient's lung pushes out gas through the tracheal tube(2) and the connector(4) into the ventilator(1). This cycle of operation is continued until a patient can start breathing on his/her own.

When the alarm condition exists, i.e. the ventilator(1) does not operate as intended, the detecting device(5) does the following actions:

a. Turn the visual and audible alarms on.
b. Shut the main section(1) of the ventilating system.
c. Open the exhaust valve(30) in the exhaust device(7).

The exhaust device(7) may not be installed in the system, since all the ventilating systems incorporate some kind of pressure release devices when the ventilator is either in expiration mode or inactive.

In accordance with the present invention, the ventilating system is provided with a main ventilating device and an auxiliary ventilating device which actuates automatically only when the main ventilating device does not operate. Accordingly, the ventilating system is very safe and reliable.

In the ventilating system, there is no locking device for connecting the connectors(3) (4) to the ventilator(1) and to the tracheal tube(2). Because of this, disconnections of the connectors may occur. In the present invention, the auxiliary ventilating device covers up most of the ventilator related failures.

The present invention may be used for ventilating breathing gas to a lung patient. Also, the ventilating system of the invention may be used for anesthesia in operation.

While the invention has been explained with reference to the specific embodiment of the invention, the explanation is illustrative and the invention is limited only by the appended claims.

What is claimed is:

1. A ventilating system adapted to supply breathing gas to a patient and exhaust used gas thereform, comprising:
    a main ventilating device including a tracheal tube adapted to be inserted into a throat of a patient, breathing gas supplying means connected to the tracheal tube to supply breathing gas to the patient, and an exhaust device attached to the tracheal tube for exhausting used gas from the ventilating device,
    a detecting device connected to the main ventilating device for detecting malfunction of the main ventilating device, said detecting device including an alarm device for alarming malfunction of the main ventilating device, a pressure sensing device for detecting pressure of a lung of the patient, and a comparator for comparing the pressure detected by the pressure sensing device and a predetermined pressure, said comparator being connected to the alarm device to eject signal thereto when value compared by the comparator is without the predetermined value, and
    an auxiliary ventilating device including a hollow tube extending along and retained inside the tracheal tube of the main ventilating device, said pressure sensing device being attached to the hollow tube to detect pressure of the lung of the patient, auxiliary breathing gas supply means connected to the hollow tube for supplying compressed breathing gas to the patient through the hollow tube separately from the breathing gas supply means of the main ventilating device, and an auxiliary exhaust device attached to the tracheal tube to exhaust breathing gas supplied to the patient from the auxiliary breathing gas supply means through the treacheal tube and the auxiliary exhaust device so that when the detecting device detects malfunction of the main ventilating device, the auxiliary ventilating device automatically actuates together with the alarm device to supply the compressed breathing gas from the auxiliary breathing gas supply means to the patient through the hollow tube and to open the auxiliary exhaust device for exhausting the used gas through the tracheal tube and the auxiliary exhaust device.

2. An auxiliary ventilating system adapted to supply breathing gas to a patient and exhaust used gas therefrom when a main ventilating device does not operate properly, said main ventilating device including a tracheal tube adapted to be inserted into a throat of a patient, breathing gas supply means connected to the tracheal tube through a connector to supply breathing gas to the patient, and an exhaust device attached to the connector for exhausting used gas from the ventilating device, said auxiliary ventilating system comprising,
    a detecting device connected to the main ventilating device for detecting malfunction of the main ventilating device, and
    an auxiliary ventilating device including a hollow tube installed inside the tracheal tube, and an auxiliary breathing gas supply means connected to the hollow tube for supplying breathing gas to the patient through the hollow tube separately from the breathing gas supply means so that when the detecting device detects malfunction of the main ventilating device, the auxiliary ventilating device automatically actuates to supply breathing gas to the patient through the hollow tube, used gas being exhausted from the patient through the tracheal tube and the connector.

3. An auxiliary ventilating system according to claim 2, further comprising an auxiliary exhaust device attached to the connector, said auxiliary exhaust device being actuated when the detecting device detects malfunction of the main ventilating device and allowing used gas supplied to the patient to exhaust from the exhaust device through the connector.

* * * * *

UNITED STATES PATENT AND TRADEMARK OFFICE
CERTIFICATE OF CORRECTION

PATENT NO.   : 5,042,470
DATED        : August 27, 1991
INVENTOR(S)  : Nozomu Kanesaka It is certified that error appears in the above-identified patent and that said Letters Patent is hereby corrected as shown below:

On the Title page

Item [76], inventor's section.

Change "Nozomi Kanesaka" to --Nozomu Kanesaka--.

Signed and Sealed this

Twenty-third Day of February, 1993

Attest:

STEPHEN G. KUNIN

*Attesting Officer*  *Acting Commissioner of Patents and Trademarks*